United States Patent
Slocum et al.

(10) Patent No.: US 8,881,594 B2
(45) Date of Patent: *Nov. 11, 2014

(54) TAPERED SPIRAL BELLOWS PRESSURE SENSOR

(76) Inventors: Alexander Henry Slocum, Bow, NH (US); Alexander H. Slocum, Jr., Bow, NH (US)

( * ) Notice: Subject to any disclaimer, the term of this patent is extended or adjusted under 35 U.S.C. 154(b) by 182 days.

This patent is subject to a terminal disclaimer.

(21) Appl. No.: 13/351,768

(22) Filed: Jan. 17, 2012

(65) Prior Publication Data

US 2013/0019689 A1 Jan. 24, 2013

Related U.S. Application Data

(60) Provisional application No. 61/449,707, filed on Mar. 6, 2011.

(51) Int. Cl.
*G01L 7/08* (2006.01)
*F16J 15/50* (2006.01)
*G01L 7/06* (2006.01)

(52) U.S. Cl.
CPC .................................. *G01L 7/061* (2013.01); *G01L 7/063* (2013.01)
USPC .......................................................... 73/715

(58) Field of Classification Search
USPC .................................. 73/700–756
See application file for complete search history.

(56) References Cited

U.S. PATENT DOCUMENTS

| | | | |
|---|---|---|---|
| 3,911,904 A | 10/1975 | Saba | |
| 4,114,458 A | 9/1978 | Alinari | |
| 4,501,273 A | 2/1985 | McGinnis | |
| 4,844,486 A | 7/1989 | Schiemann | |
| 4,966,035 A | 10/1990 | Huang | |
| 5,103,670 A | 4/1992 | Wu et al. | |
| 5,336,183 A | 8/1994 | Greelis et al. | |
| 5,439,178 A | 8/1995 | Peterson | |
| 5,722,955 A | 3/1998 | Racz | |
| 5,935,084 A | 8/1999 | Southworth | |
| 6,042,092 A | 3/2000 | Shibata | |
| 6,485,471 B1 | 11/2002 | Zivitz et al. | |
| 7,018,359 B2 | 3/2006 | Igarashi et al. | |
| 7,383,736 B2 | 6/2008 | Esnouf | |
| 8,291,768 B2* | 10/2012 | Spiegel et al. | 73/700 |
| 8,397,577 B2* | 3/2013 | Slocum et al. | 73/715 |
| 2010/0179488 A1* | 7/2010 | Spiegel et al. | 604/240 |
| 2011/0125107 A1* | 5/2011 | Slocum et al. | 604/272 |

(Continued)

FOREIGN PATENT DOCUMENTS

EP 1195545 A2 4/2002

*Primary Examiner* — Andre Allen
(74) *Attorney, Agent, or Firm* — Rajesh Vallabh; Foley Hoag LLP

(57) ABSTRACT

A pressure measuring device includes a resilient expandable pressure sensor element having an open end and an opposite closed end. The pressure sensor element includes spiral flutes extending between the open and closed ends defining spiral bellows. The pressure sensor element is tapered over at least a portion of its length from the open end to the closed end. The pressure measuring device also includes a supporting structure having a pressure indicating scale. The supporting structure holds the pressure sensor element such that the open end of the pressure sensor element is in communication with a fluid whose pressure is to be measured and pressure applied by the fluid causes the pressure sensor element to expand axially and be visibly displaced relative to the pressure indicating scale by a distance related to the pressure applied by the fluid.

23 Claims, 9 Drawing Sheets

(56) References Cited

U.S. PATENT DOCUMENTS

2011/0251579 A1* 10/2011 Aklog et al. ................. 604/500
2012/0302957 A1* 11/2012 Vlodaver et al. ............. 604/151
2012/0312100 A1* 12/2012 Slocum ......................... 73/732
2012/0312300 A1* 12/2012 Spiegel et al. ........... 128/202.22

* cited by examiner

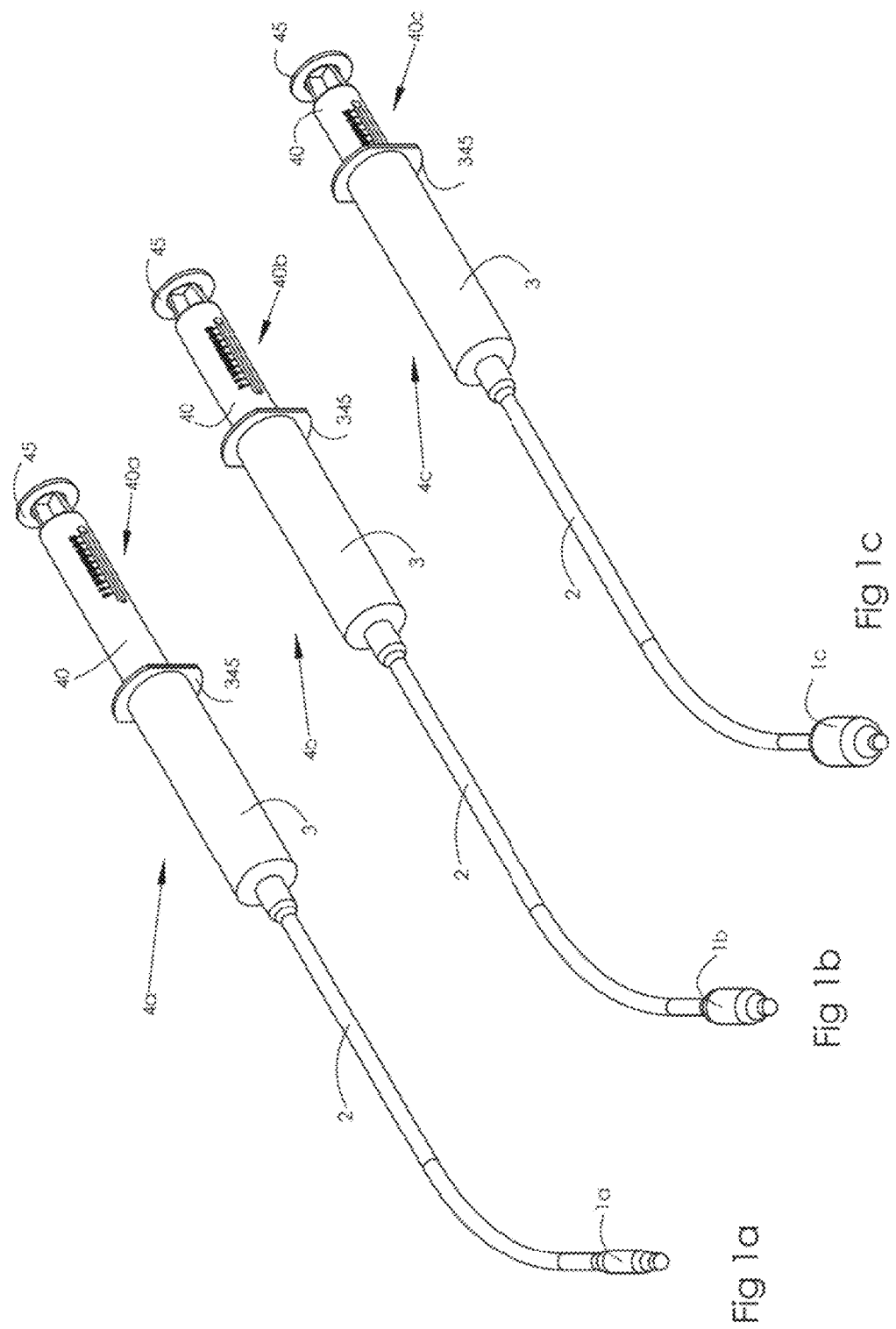

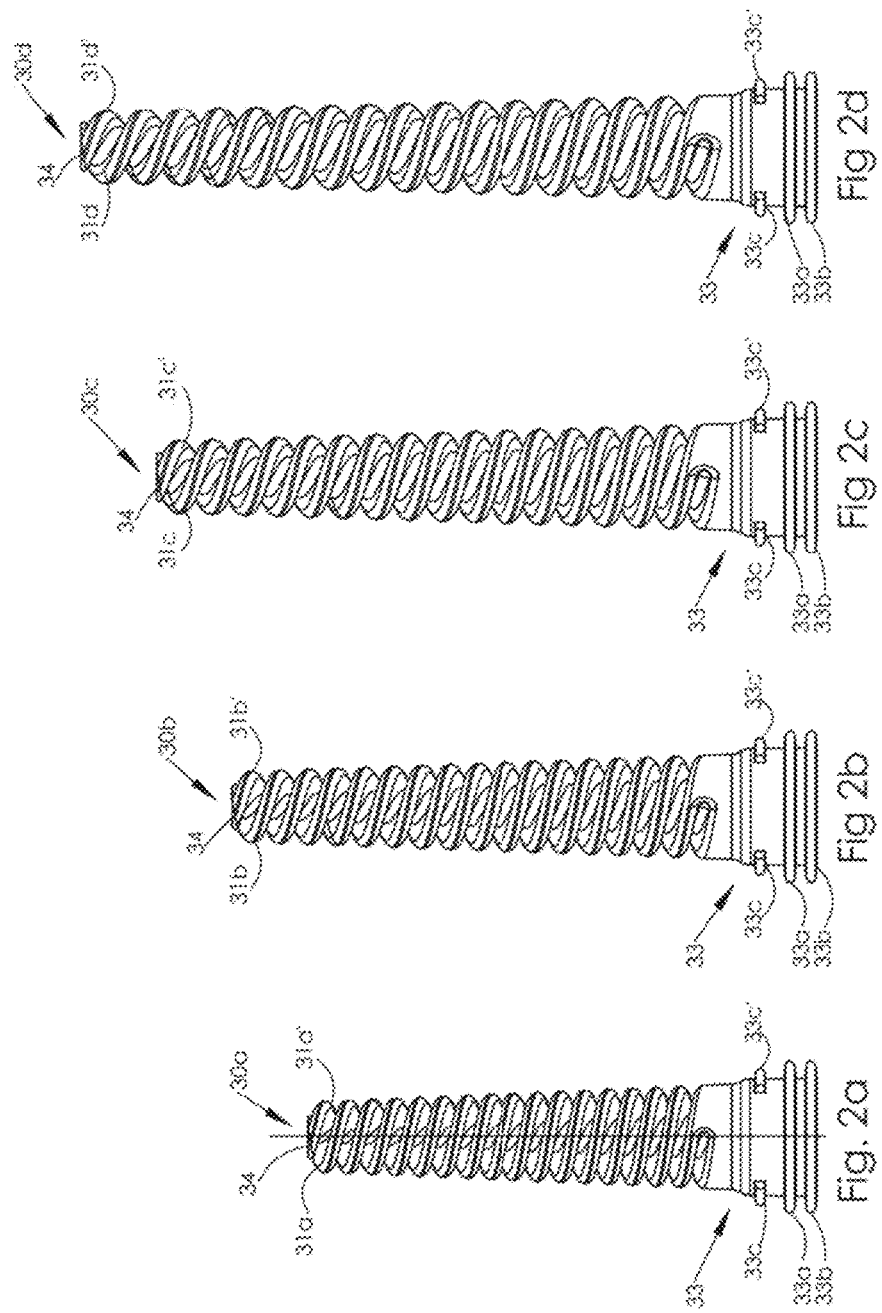

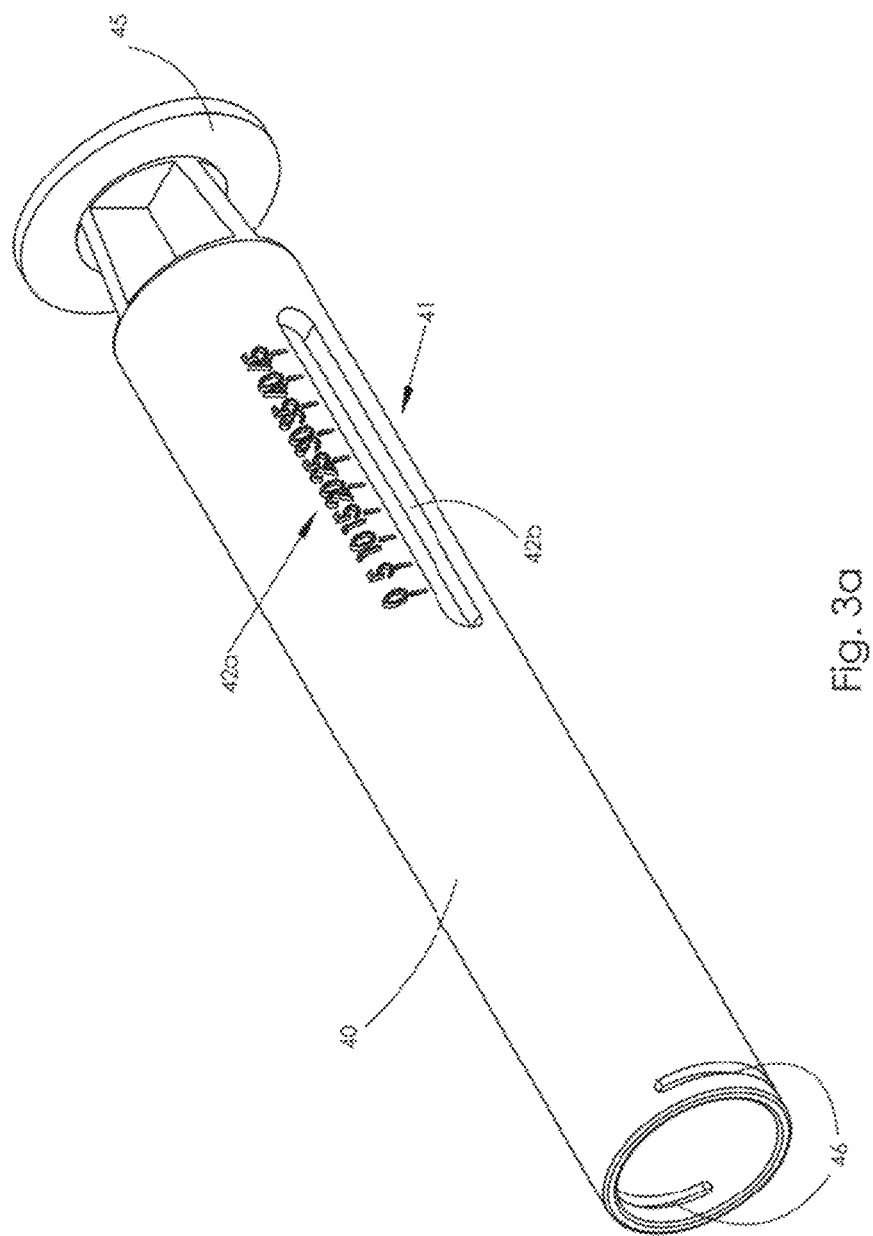

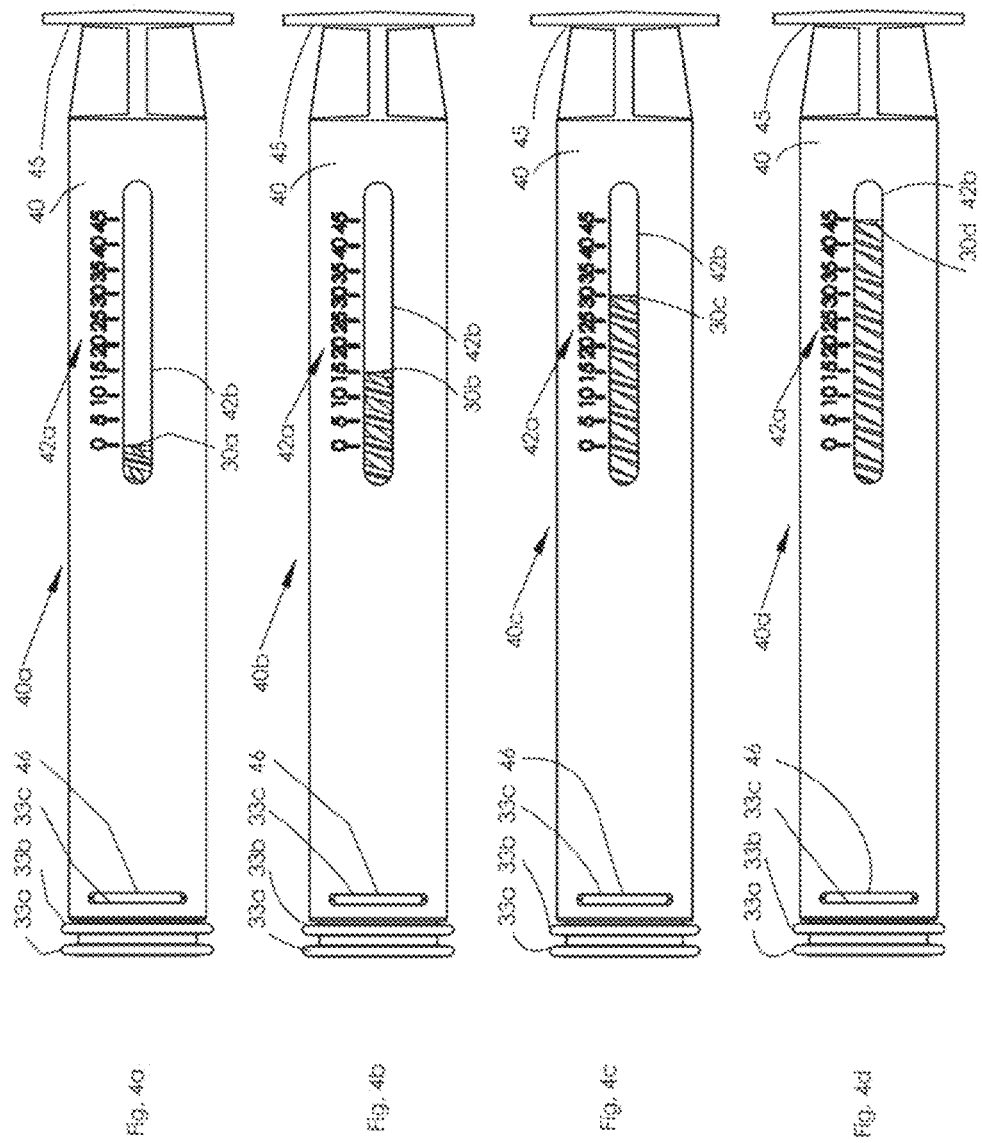

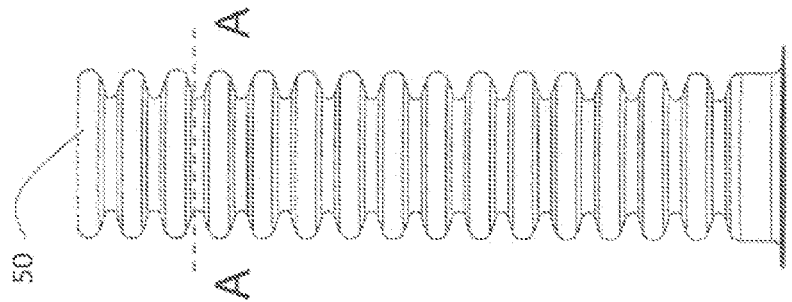
Fig. 5a
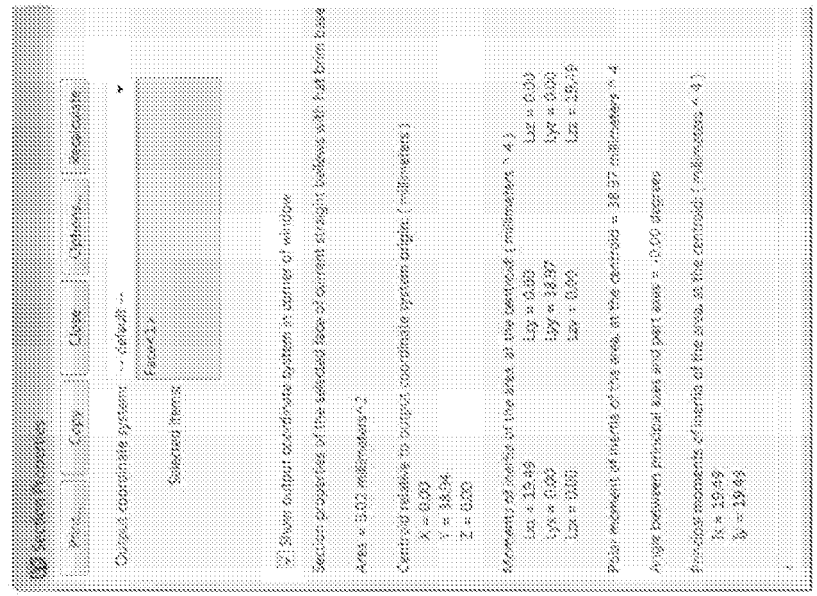
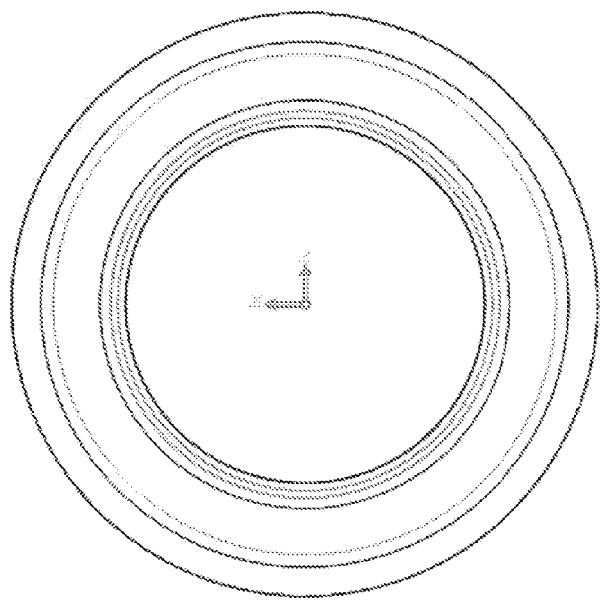
Section A-A
Fig. 5b

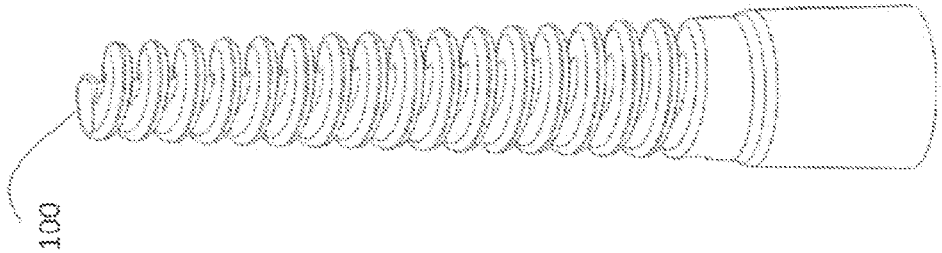
Fig. 6a
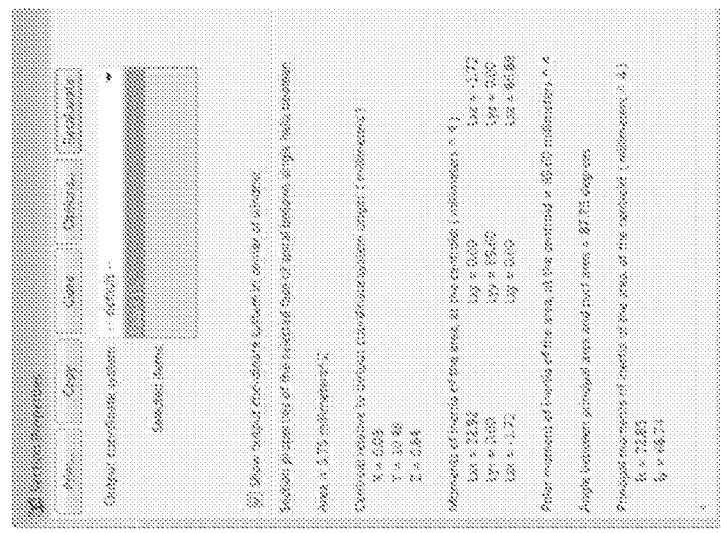
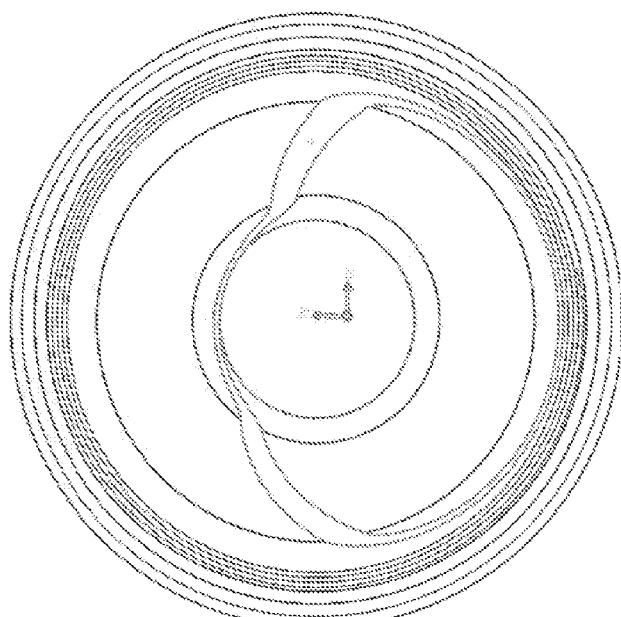
Fig. 6b

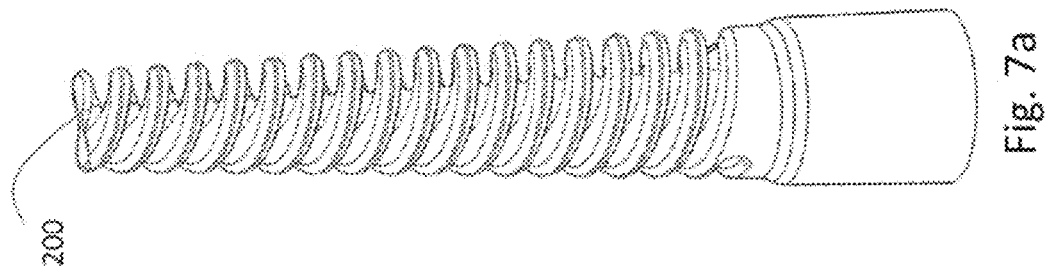
Fig. 7a
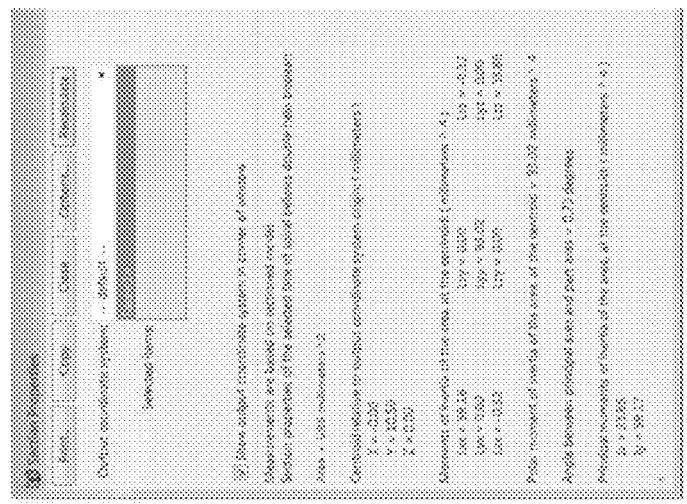
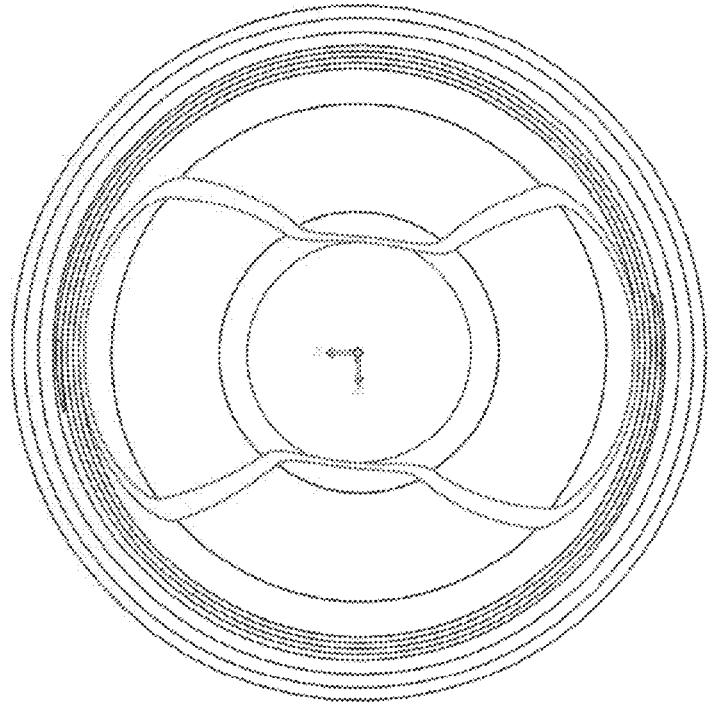
Fig. 7b

TAPERED SPIRAL BELLOWS PRESSURE SENSOR

CROSS REFERENCE TO RELATED APPLICATION

This application claims priority from U.S. Provisional Patent Application No. 61/449,707, filed on Mar. 6, 2011, entitled TAPERED SPIRAL BELLOWS PRESSURE SENSOR, which is hereby incorporated by reference.

BACKGROUND

The present application relates generally to pressure indicating devices. More particularly, it relates to a device with a tapered spiral bellows pressure sensor element, where the pressure to be measured causes a predominantly axial displacement of the bellows, which can be observed and correlated to the amount of pressure.

Many instruments for measuring pressure rely on the pressure causing a mechanical deformation of a resilient mechanical structure such as bellows. The deformation of the structure causes an indicator to move, allowing a user to observe a value for the amount of pressure. In some fields, such as medical devices or fields in which an extreme purity of gases must be maintained, it is important to be able to measure pressure with a single element that can be made from a material compatible with the application.

Bellows can be used to measure pressure through visual monitoring of the extension of the bellows. However, bellows are difficult to manufacture with walls thin enough for accurately measuring very low pressures. Moreover, variations in wall thickness during manufacturing can lead to significant variations in accuracy. For instance, a 10% variation in wall thickness of conventional cylindrical bellows can lead to 20% or more variation in pressure indicated depending on the design of the bellows' convolutions. One of the causes of wall thickness variation is the difficulty with which the convolutions are made; most bellows are made using blow molding or injection molding, which often does not lead to accurate wall thickness, particularly in corners. Errors in thickness in the corners leads to variation in effective diameter. The diameter of a plate, which the convolution effectively is with regard to predicting compliance, varies with the diameter squared. Material thickness variation in the acute angle of the corners where two convolutions meet is typically much greater than the thickness variation on the plate region; hence it causes a more significant variation in the effective plate diameter and hence compliance of the bellows. This makes accurate measurement of very small pressures, e.g., on the order of millibar to centibars, very difficult.

When a bellows is injection molded, greater thickness control can be achieved. However, removing bellows from molds without breaking the bellows can be difficult. Additionally, it is difficult to make bellows thin enough using molding for accurate low pressure measurement.

A further difficulty with bellows is the potential for sliding mechanical contact with the supporting instrument body, and friction is notoriously non-repeatable, which gives further rise to variations in pressure measurement readings, particularly at low pressures.

BRIEF SUMMARY OF THE DISCLOSURE

A pressure measuring device in accordance with one or more embodiments includes a resilient spiral bellows pressure sensor element having an open end and an opposite closed end. The pressure sensor element includes spiral flutes extending between the open and closed ends defining spiral bellows. The pressure sensor element is tapered over at least a portion of its length from the open end to the closed end. The pressure measuring device also includes a supporting structure having a pressure indicating scale. The supporting structure holds the pressure sensor element such that the open end of the pressure sensor element is in communication with a fluid whose pressure is to be measured, and pressure applied by the fluid causes the pressure sensor element to expand axially and be visibly displaced relative to the pressure indicating scale by a distance related to the pressure applied by the fluid.

A pressure measuring syringe in accordance with one or more embodiments includes a syringe barrel and a syringe plunger including an end proximal to a user that can be manipulated by the user and an opposite distal end slidably disposed in the syringe barrel. The syringe plunger includes a pressure indicating scale. A resilient spiral bellows pressure sensor element is disposed in the syringe plunger. The pressure sensor element has an open end and an opposite closed end. The pressure sensor element includes spiral flutes extending between the open and closed ends defining spiral bellows. The pressure sensor element is tapered over at least a portion of its length from the open end to the closed end. The open end of the pressure sensor element is attached to an open end of the syringe plunger distal to the user such that the open end of the pressure sensor element is in communication with a fluid whose pressure is to be measured and pressure applied by the fluid causes the pressure sensor element to expand axially and be visibly displaced relative to the pressure indicating scale by a distance related to the pressure applied by the fluid.

A method of making a pressure sensor in accordance with one or more embodiments includes forming a resilient spiral bellows pressure sensor element in a mold. The pressure sensor element includes an open end and an opposite closed end. The pressure sensor element has spiral flutes extending between the open and closed ends defining spiral bellows. The pressure sensor element is tapered over at least a portion of its length from the open end to the closed end. The method further comprises removing the pressure sensor element from the mold by unthreading a mold core from the mold, and attaching the open end of the pressure sensor element to a supporting structure having a pressure scale. When the open end of the pressure sensor element is placed in communication with a fluid whose pressure is to be measured, pressure applied by the fluid causes the pressure sensor element to axially expand and be visibly displaced relative to the pressure indicating scale by a distance related to the pressure applied by the fluid.

BRIEF DESCRIPTION OF THE DRAWINGS

FIGS. 1a-1c are isometric views of a pressure sensing syringe including a tapered spiral bellows pressure sensor element in accordance with one or more embodiments. FIGS. 1a-1c illustrate operation of the syringe to inflate a balloon such as an endotracheal cuff. FIGS. 1a-1c show no inflation, partial inflation, and full inflation of the endotracheal cuff, respectively.

FIGS. 2a-2d are front views of a double helix tapered spiral bellows pressure sensor element in accordance with one or more embodiments. FIGS. 2a-2d show the state of the sensor element under applied pressures of 0 cm $H_2O$, 15 cm $H_2O$, 30 cm $H_2O$, and 45 cm $H_2O$, respectively.

FIG. 3a is an isometric view of a syringe plunger in accordance with one or more embodiments in which a tapered spiral bellows pressure sensor element can be installed.

FIGS. 4a-4d are side views illustrating a syringe plunger and tapered spiral bellows pressure sensor element assembly in accordance with one or more embodiments. FIGS. 4a-4d show the state of the sensor under applied pressures of 0 cm $H_2O$, 15 cm $H_2O$, 30 cm $H_2O$, and 45 cm $H_2O$, respectively.

FIG. 5a is a side view of a conventional bellows. FIG. 5b provides a cross section view through the bellows of FIG. 5a at a minor diameter and a corresponding section properties table.

FIG. 6a is an isometric view of a single helix spiral bellows. FIG. 6b provides a cross section view through the bellows of FIG. 6a at a minor diameter near the base and a corresponding section properties table.

FIG. 7a is an isometric view of a double helix spiral bellows. FIG. 7b provides a cross section view through the bellows of FIG. 7a at a minor diameter near the base and the corresponding section properties table.

Like or identical reference numbers are used to identify common or similar elements.

DETAILED DESCRIPTION

Figure 3B:
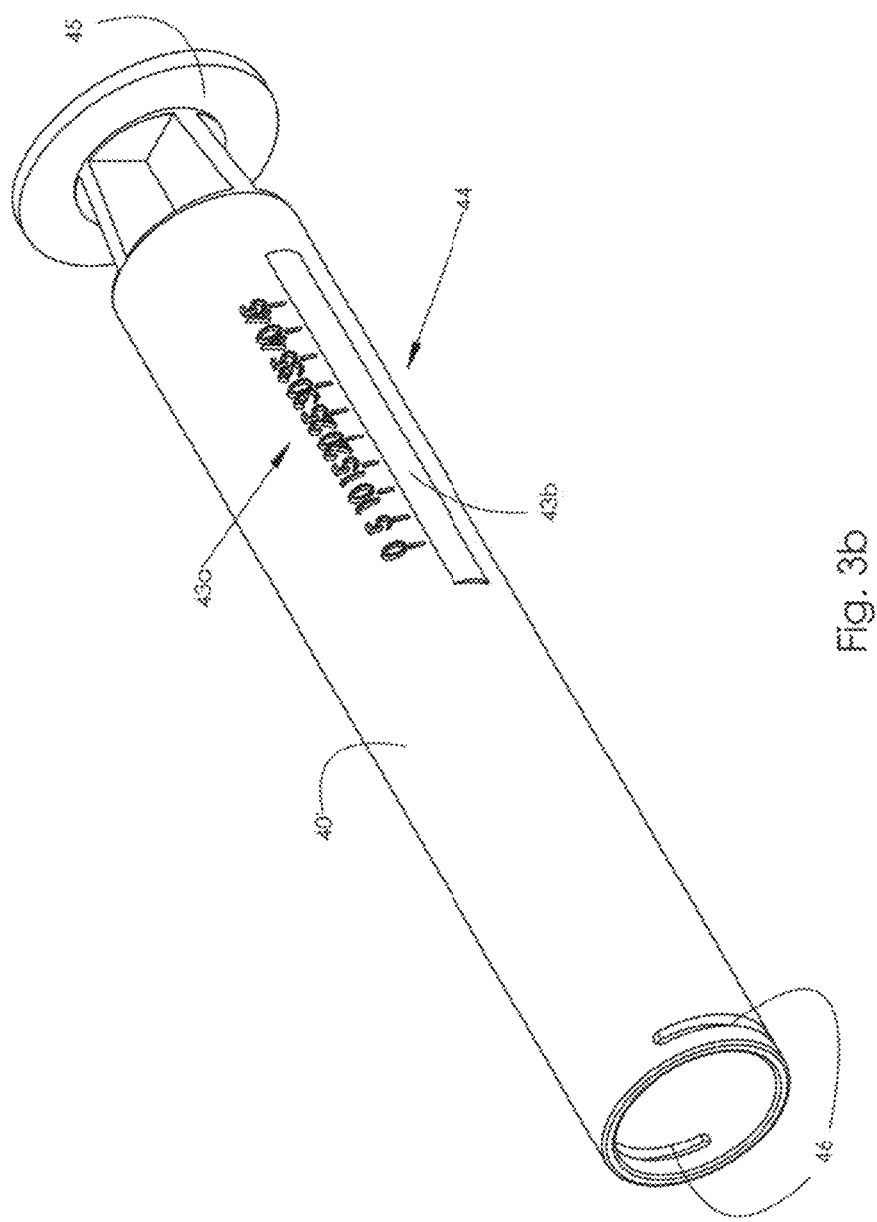
FIG. 3b is an isometric view of an alternate syringe plunger with a magnification feature in accordance with one or more embodiments in which a tapered spiral bellows pressure sensor element can be installed.

Various embodiments disclosed herein are directed to pressure measuring devices including a resilient spiral bellows pressure sensor element. The pressure sensor element includes an open end and an opposite closed end, and spiral flutes extending between the open and closed ends defining spiral bellows. The pressure sensor element is tapered over at least a portion of its length from the open end to the closed end. A supporting or enshrouding structure having a pressure indicating scale holds the pressure sensor element such that the open end of the pressure sensor element is in communication with a fluid whose pressure is to be measured. Pressure applied by the fluid causes the pressure sensor element to expand axially and be visibly displaced relative to the pressure indicating scale by a distance related to the pressure applied by the fluid. In some embodiments, the supporting structure forms a plunger for a pressure measuring syringe.

The pressure sensor element bellows have sufficiently deep convolutions so as to have generally high axial compliance (low axial stiffness). The bellows however are sufficiently laterally stiff so that when gravity is transverse to the bellows' axis, the bellows will not droop so much as to adversely affect the pressure reading, and also to resist other parasitic transverse forces, e.g. due to friction.

The convolutions of the spiral bellows are formed by helical thread forms (e.g., a double or triple start thread) such that for any cross section, the 2nd moment of the area (i.e., the bending moment of inertia) is relatively high, while maintaining high axial compliance so it makes the bellows sensitive to internal pressure, but less sensitive to parasitic gravitational and frictional forces.

The pressure sensor element is tapered over its length to increase the ease with which it can be manufactured and to decrease the likelihood that radial displacements could cause the tip of the bellows to touch and drag against the wall of an enshrouding chamber.

The pressure sensor element is thus configured such that when held in any orientation, it will either not contact the sidewall of an enshrouding support structure or will do so with minimal force to minimize the occurrence of parasitic friction forces that can cause pressure measurement errors.

The pressure indicating devices can have a broad range of applications including, e.g., in medical devices, and as a dynamic fluid capacitive element in precision fluid instruments. In semiconductor and pharmaceutical manufacturing where process gasses must often have precise pressure control, the device can provide a quick visual indicator of pressure while also acting as a dynamic capacitive element to help control pressure.

In one particular example illustrated in the drawings, tapered spiral bellows pressure sensor elements in accordance with one or more embodiments are implemented in syringes used to inflate an endotracheal tube (ET) cuff when a patient is intubated. Such syringes typically have a barrel inside diameter of about 16 mm and a length of about 75 mm. It should be understood that the tapered spiral bellows pressure sensor elements are scalable to a variety of other applications and pressures including, without limitation, for inflation of cuffs for pediatric and neonatal ET tubes. Furthermore, tapered spiral bellows pressure sensor elements can have a variety of non-medical device applications, as indicated above.

In a preferred embodiment shown in FIGS. 1a, 1b, and 1c and FIGS. 4a, 4b, and 4c (which show just the plunger/bellows subassembly), a pressure sensing syringe 4 is respectively shown in states 4a, 4b, and 4c of not inflating, partially inflating, and fully inflating a balloon such as an endotracheal cuff (balloons 1a, 1b, and 1c), respectively. FIG. 4d shows an over-inflated state of 45 cm of $H_2O$. The barrel 3 of the syringe 4 is connected via a tube 2 to the balloon 1 (1a, 1b, 1c) by tube 2. Flange 345 on the barrel 3 resists an opposing force that would be applied to syringe plunger 40 end 45. In different stages of inflation from uninflated (4a) to partially inflated (4b) to fully inflated (4c), the sensor areas 40a, 40b, and 40c, respectively, advance with the syringe plunger assembly 40a, 40b, and 40c.

FIGS. 2a, 2b, 2c, and 2d show the tapered spiral bellows sensor 30 in its uninflated (0 cm $H_2O$) state 30a and various inflation (15 cm, 30 cm, and 45 cm $H_2O$) states 30a, 30b, 30c, and 30d, respectively. The sensor 30 has a base 33 that has sealing rings 33a and 33b, and snap-fit protrusions 33c and 33c'. Spiral flutes 31a and 31a' form a double helix and taper from the base 33 to the distal end 34, which is flat for easier reading of the indicated pressure. The depth of these spiral flutes (helical convolutions) is shown to be common along their length, but could taper and still the core could be removed from molding as long as the pitch was constant. By way of example, for the application of the sensor 30 in a pressure sensing syringe for inflating an endotracheal cuff, the base 33 where the flutes start is about 11 mm in diameter, and the vertical height of the flutes is 50 mm and tapers to a distal end diameter of about 7.5 mm. The wall thickness of the rubber is 0.1 mm, but could be as thick as 0.15 mm. In the former case, the bellows will expand about 24 mm under 45 cm $H_2O$ pressure if a soft rubber, such as a silicone rubber, with an elastic modulus on the order of 10,000 $N/m^2$ is used.

As the bellows expands axially under pressure, the depth of flutes decreases and their pitch increases as they stretch under the internal pressure. Flutes 31b and 31b' correspond to about 15 cm H$_2$O; flutes 31c and 31c' correspond to about 30 cm H$_2$O, and flutes 31d and 31d' correspond to about 45 cm H$_2$O.

FIG. 3a shows an exemplary enshrouding structure 40 (also referred to as the plunger in a syringe application) in accordance with one or more embodiments. It has slits 46 near its base that axially and rotationally constrain the bellows of FIGS. 2a, 2b, 2c, and 2d via the bellows' snap-fit tabs 33c and 33c'. The sensor region 41 includes a slot 42b, which is not needed if the plastic is very clear, and a scale 42a, which can be molded integral or inked on or even be a label applied to the surface of the plunger during the manufacturing process. Only one side is shown here, and for ergonomic reasons, multiple sets placed circumferentially around the structure 40 body can be used. The sensor region is located and scaled in accordance with the bellows' sensitivity and size. Shown here, it is sized and labeled to indicate centimeters of water pressure (cm H$_2$O). Note that the sensor region 41 (and its mirror image) is aligned with the slots 46 so the part can easily be molded with two halves and a simple core.

FIG. 3b shows an enshrouding structure 40' (also referred to as the plunger in a syringe application) in accordance with one or more alternate embodiments. It also has slits 46 near its base that axially and rotationally constrain the bellows of FIGS. 2a, 2b, 2c, and 2d via the bellow's snap-fit tabs 33c and 33c'. The sensor region 44 includes cylindrical lens structures 43b that help magnify the end position of the bellows and makes it easier to read the position of the end of the bellows with respect to the scale 43a. The scale 43a, which can be molded integral or inked on or even be a label applied as part of the manufacturing process. Only one side is shown here, and for ergonomic reasons, multiple sets placed circumferentially around the structure 40' body can be used. The sensor region is located and scaled in accordance with the bellows' sensitivity and size. Shown here, it is sized and labeled to indicate centimeters of water pressure (cm H$_2$O). Note that the sensor region 44 (and its mirror image) is aligned with the slots 46 so the part can easily be molded with two halves and a simple core.

Figure 8A:
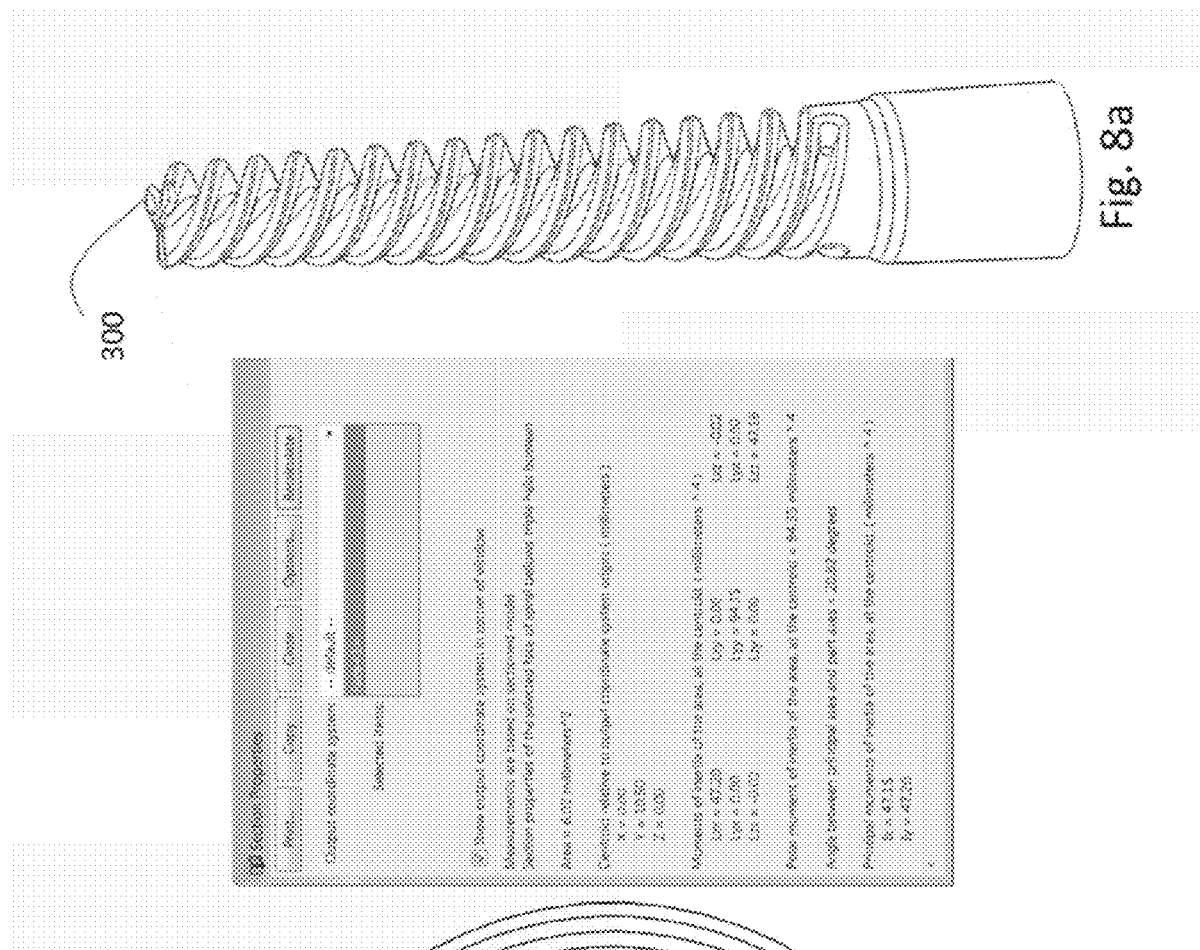
FIG. 8a is an isometric view of a triple helix spiral bellows.
Figure 8B:
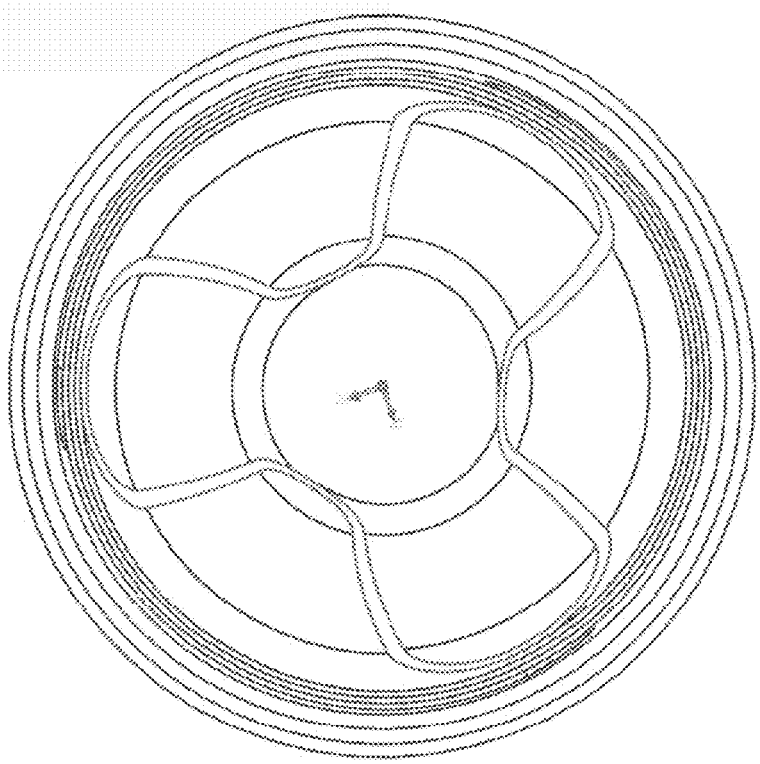
FIG. 8b provides a cross section view through the bellows of FIG. 8a at a minor diameter near its base and the corresponding section properties table.

It is useful to compare exemplary tapered spiral bellows in accordance with one or more embodiments to a conventional circular cross section bellows. FIG. 5a is side view of a conventional bellows 50 with circular cross section convolutions. FIG. 5b is a cross section through the bellows 50 at a minor diameter and provides the corresponding section properties table. FIG. 6a is an isometric view of a single helix spiral bellows 100 with spiral convolutions. FIG. 6b is a cross section through the bellows 100 at a minor diameter near the base and provides the corresponding section properties table. FIG. 7a is an isometric view of a double helix spiral bellows 200 with double helix convolutions. FIG. 7b is a cross section through the bellows 200 at a minor diameter near the base and provides the corresponding section properties table. FIG. 8a is an isometric view of a triple helix spiral bellows 300 with triple helix convolutions. FIG. 8b is a cross section through the bellows 300 at a minor diameter near its base and the corresponding section properties table.

Finite element analysis of these bellows can be used to determine a bellows' axial compliance (extension) under internal pressure and also their lateral (potentially parasitic) compliance due to gross asymmetries in structure. Although the single helix bellows may seem to be a reasonable candidate based on high axial compliance, which is desirable for pressure sensing, its inherent large asymmetry in cross section, due to the single convolution, means that it will curve considerably and drag against the walls of an enshrouding structure. For symmetrical bellows, a figure of merit regarding parasitic radial motion, and hence potential drag against the cylinder, is the cross sectional area and the second moment of the area ("moment of inertia") with respect to the neutral axis (in this case of a symmetrical cross section, about the centroid).

In the case of a typical cylindrical bellows, the outside diameter being 11 mm and the depth of convolutions about 2 mm (7 mm ID), a strain of 57% results from removing the bellows from the mold. Much more and the rubber would risk tearing or forming pinhole tears, which would render it useless for pressure sensing. In the case of the helical bellows, particularly since a taper over the length of a few (e.g., 1-4) degrees included angle (so it tapers from about 11 mm at the base to 7.5 mm at the tip) enables the core to be easily rotated (unthreaded) from the mold and hence a deeper convolution can be used. In this case, the depth is 3 mm. The convolution width is 3 mm whereas the pitch is equal to the product of the convolution width and the number of helical convolutions (i.e., thread starts, so 6 mm for a double helix bellows), and hence the strain to remove the bellows is negligible as it is "unthreaded" off of the core. For a helical bellows, the smaller the pitch, the smaller the helix angle and hence the greater the compliance by an amount more significant than simply decreasing the pitch with a cylindrical bellows. For reference, the cylindrical bellows of FIG. 5a can be thought of as having a pitch angle of zero.

In both cases, to decrease the difficulty of mold manufacture, the included angle of the convolution sides is about between 3 and 15 degrees. For a change from 15 degrees to 10 degrees included angle and a convolution depth of 3 mm, the convolution width decreases from 3 mm to 2.75 mm. The smaller the included angle, the smaller the pitch and hence the greater the axial compliance for a given length bellows. However, manufacturability is of prime importance rather than trying to obtain the very last bit of compliance, and hence convolution depth and width being equal and from ⅓rd to ¼th the nominal diameter at the base of the bellows is quite reasonable, which allows for a relatively more easily manufactured included angle of 15 degrees. Near the tip, the ratio may be as small as ½ to ⅓rd of the diameter. The other features that help increase ease of manufacture and hence also maintain more precise control over bellows wall thickness, which is required for bellows accuracy, are the rounded corners of the convolutions. Sharp corners are to be avoided for reasons of stress concentration and also thickness uniformity during molding. The corner radii are typically ⅕th to ⅙th the convolution width, so in the case of the helical bellows, about 0.3-0.7 mm.

The spiral bellows in accordance with various embodiments are also tapered to not only facilitate removing the core from the molded part, but to help reduce the risk that the bellows will touch the wall of an enshrouding structure, such as a plastic tube, either due to gravity or from any asymmetry in manufacture, which when subjected to internal pressure would cause the bellows to curve as it axially deforms. The slight taper, on the other hand, has negligible effect on overall axial compliance and sensitivity, whereas if it touched the enshrouding cylinder wall, friction would cause significant drag force resulting in inaccuracies in pressure measurement and subsequent reading by the user. Table 1 below illustrates how the taper helps to maintain the tip of the double helix away from the enshrouding wall even under gravity loading and a large 5% manufacturing asymmetry, which effectively would cause the pressure forces to act eccentrically from the effective center of stiffness of the bellows.

TABLE 1

| | | |
|---|---|---|
| pressure (cm H2O) | 0 | 30 |
| length (mm) | 40 | 58 |
| weight per unit length (N) | 5.9E−05 | 4.1E−05 |
| moment of inertia at base (mm^4) | 47.2 | 32.6 |
| elastic modulii (N/mm^2) | 6.1 | 6.1 |
| tip deflection (mm) | 0.065 | 0.199 |
| Effective axial force at full pressure (N) | | 0.279 |
| assumed load assymetry | | 5% |
| resulting moment (N-mm) | | 0.077 |
| resulting radial deflection (mm) | | 0.651 |
| maximum total radial deflection (mm) | | 0.850 |

For these calculations, the moment of inertia is scaled with the increase in length as the inner diameter will decrease somewhat (although not as much as the outer diameter) and the minor moment of inertia is dominated by the nominal inside diameter. The reason beam bending analysis is used instead of finite element analysis is that the former requires a very powerful computer to mesh the entire length of the bellows, and even a machine with 16 GB of RAM typically fails to be able to mesh the entire bellows (where it can mesh just a 9 mm long section-barely-with a fine enough mesh to give accurate results). The spreadsheet calculations using beam theory are fast and easy to scale and play "what-if" design scenarios with, and this shows how the taper is important to keep the tip from touching the wall of the enshrouding structure. One could ask "why not make the entire length of the bellows smaller diameter", and the answer is that the thicker base helps increase axial compliance and greatly increases radial bending resistance, by allowing for larger taper.

Hence for preferred embodiments, the above demonstrates a design method to ascertain the degree of taper: the taper to be used is the larger of that required to generally prevent contact with the wall of an enshrouding structure, or that required to ease release from a mold. In the case of a cylindrical bellows, the latter is not typically going to make that big of a difference (it will be difficult regardless), but in the case of a spiral bellows where the core is rotated out of the mold, even a taper of a fraction of a degree can help, and a taper of a few degrees will help significantly more with manufacturing and to provide tip clearance, while having only a small negative effect on bellows axial compliance (sensitivity for pressure measurement).

The tapered bellows can be incorporated into the plunger of a syringe where high sealing forces can not only provide an excellent seal, but can maintain plunger position when finger forces are removed from the plunger. Since the bellows is in effect parallel with the plunger with its distal end substantially free from contact with its enshrouding structure, the bellows will primarily experience forces created by the air pressure on the bellows and thus give a true and accurate pressure reading proportional to its extension.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments.

Additionally, elements and components described herein may be further divided into additional components or joined together to form fewer components for performing the same functions.

Accordingly, the foregoing description and attached drawings are by way of example only, and are not intended to be limiting.

What is claimed is:

1. A pressure measuring device, comprising:
   a resilient expandable pressure sensor element having an open end and an opposite closed end, the pressure sensor element having spiral flutes extending between the open and closed ends defining spiral bellows, and the pressure sensor element being tapered over at least a portion of its length from the open end to the closed end; and
   a supporting structure having a pressure indicating scale, the supporting structure holding the pressure sensor element such that the open end of the pressure sensor element is in communication with a fluid whose pressure is to be measured, and pressure applied by the fluid causes the pressure sensor element to expand axially and be visibly displaced relative to the pressure indicating scale by a distance related to the pressure applied by the fluid.

2. The pressure measuring device of claim 1, wherein the spiral flutes form double or triple helix spiral bellows.

3. The pressure measuring device of claim 1, wherein the depth of the spiral flutes varies along the length of the pressure sensor element, and wherein the pitch of the spiral flutes is generally constant along the length of the pressure sensor element.

4. The pressure measuring device of claim 1, wherein the pressure indicating scale includes one or more pressure value indicators.

5. The pressure measuring device of claim 1, wherein the pressure sensor element comprises rubber.

6. The pressure measuring device of claim 1, wherein the supporting structure enshrouds the pressure sensor element and comprises a generally clear material enabling a user to view displacement of the pressure sensor element in the supporting structure.

7. The pressure measuring device of claim 1, wherein the supporting structure includes a magnification element to enhance a user's view of the displacement of the pressure sensor element in the supporting structure.

8. The pressure measuring device of claim 1, wherein the supporting structure comprises a plunger of a pressure measuring syringe, and wherein the pressure measuring syringe further comprises an outer syringe barrel into which the plunger moves, and fluid seals between the plunger and the barrel.

9. The pressure measuring device of claim 8, wherein sealing forces between the plunger and the outer syringe barrel of the syringe create static friction forces to maintain axial position of the plunger when user finger forces are removed from the plunger.

10. The pressure measuring device of claim 1, wherein the open end of the pressure sensor element includes one or more protrusions engaged by one or more openings in the supporting structure.

11. The pressure measuring device of claim 1, wherein the open end of the pressure sensor element includes one or more sealing rings engaging an inner wall of the supporting structure.

12. A pressure measuring syringe, comprising:
   a syringe barrel;
   a syringe plunger including an end proximal to a user that can be manipulated by the user and an opposite distal end slidably disposed in the syringe barrel, the syringe plunger including a pressure indicating scale; and a resilient expandable pressure sensor element disposed in the syringe plunger, the pressure sensor element having an open end and an opposite closed end, the pressure sensor element having spiral flutes extending between the open and closed ends defining spiral bellows, and the pressure sensor element being tapered over at least a portion of its length from the open end to the closed end, the open end of the pressure sensor element being attached to an open end of the syringe plunger distal to the user such that the open end of the pressure sensor element is in communication with a fluid whose pressure is to be measured and pressure applied by the fluid causes the pressure sensor element to expand axially and be visibly displaced relative to the pressure indicating scale by a distance related to the pressure applied by the fluid.

13. The pressure measuring syringe of claim 12, wherein the spiral flutes form double or triple helix spiral bellows.

14. The pressure measuring syringe of claim 12, wherein the depth of the spiral flutes varies along the length of the pressure sensor element, and wherein the pitch of the spiral flutes is generally constant along the length of the pressure sensor element.

15. The pressure measuring syringe of claim 12, wherein the syringe is adapted to inflate an endotracheal tube cuff.

16. The pressure measuring syringe of claim 12, wherein the pressure indicating scale includes one or more pressure value indicators.

17. The pressure measuring syringe of claim 12, wherein the pressure sensor element comprises rubber.

18. The pressure measuring syringe of claim 12, wherein the plunger comprises a material enabling a user to view displacement of the rolling diaphragm portion held by the plunger.

19. The pressure measuring syringe of claim 12, wherein the plunger includes a magnification element to enhance a user's view of the displacement of the rolling diaphragm portion held by the plunger.

20. The pressure measuring syringe of claim 12, wherein sealing forces between the plunger and the syringe barrel create static friction forces to maintain axial position the plunger when user finger forces are removed from the plunger.

21. The pressure measuring syringe of claim 12, wherein the open end of the pressure sensor element includes one or more protrusions held by one or more openings in the plunger.

22. The pressure measuring syringe of claim 12, wherein the open end of the pressure sensor element includes one or more sealing rings engaging an inner wall of the plunger.

23. A method of making a pressure sensor, comprising the steps of:

forming a resilient expandable pressure sensor element in a mold, the pressure sensor element having an open end and an opposite closed end, the pressure sensor element having spiral flutes extending between the open and closed ends defining spiral bellows, and the pressure sensor element being tapered over at least a portion of its length from the open end to the closed end;

removing the pressure sensor element from the mold by unthreading a mold core from the mold; and attaching the open end of the pressure sensor element to a supporting structure having a pressure scale, wherein when the open end of the pressure sensor element is placed in communication with a fluid whose pressure is to be measured, pressure applied by the fluid causes the pressure sensor element to axially expand and be visibly displaced relative to the pressure indicating scale by a distance related to the pressure applied by the fluid.

* * * * *